(12) United States Patent
Kleen

(10) Patent No.: US 7,706,585 B2
(45) Date of Patent: Apr. 27, 2010

(54) METHOD AND APPARATUS TO DETECT THE ROUGHNESS OF VESSELS

(75) Inventor: Martin Kleen, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 1160 days.

(21) Appl. No.: 10/860,933

(22) Filed: Jun. 4, 2004

(65) Prior Publication Data

US 2005/0004445 A1 Jan. 6, 2005

(30) Foreign Application Priority Data

Jun. 4, 2003 (DE) ................................ 103 25 298

(51) Int. Cl.
*G06K 9/00* (2006.01)
(52) U.S. Cl. ..................................................... 382/128
(58) Field of Classification Search ................ 430/40.5; 435/40.5; 702/19; 382/128; 600/407
See application file for complete search history.

(56) References Cited

U.S. PATENT DOCUMENTS

| | | | |
|---|---|---|---|
| 6,264,609 B1 * | 7/2001 | Herrington et al. | 600/443 |
| 6,278,767 B1 * | 8/2001 | Hsieh | 378/163 |
| 6,301,498 B1 * | 10/2001 | Greenberg et al. | 600/425 |
| 6,466,687 B1 * | 10/2002 | Uppaluri et al. | 382/128 |
| 6,835,177 B2 * | 12/2004 | Fritz et al. | 600/443 |
| 2002/0086347 A1 * | 7/2002 | Johnson et al. | 435/40.5 |
| 2002/0106116 A1 * | 8/2002 | Knoplioch et al. | 382/128 |
| 2006/0147897 A1 * | 7/2006 | Grinvald et al. | 435/4 |

OTHER PUBLICATIONS

"Biostatistics," Norman et al, Chapter I ("The Basics") (2000), pp. 2-5.
"Significance of the Angiographic Morphology of Localized Coronary Stenoses: Histophathologic Correlations," Levin, Circulation, vol. 66, No. 2 (1982), pp. 316-320.
"Bausteine des Chaos: Fraktale," Saupe (1998), pp. 233-245.
"Die Fraktale Geometrie der Natur," Mandelbrot, Chapter 3 (Dimension, Symmetrie, Divergenz) (1991) pp. 26-31.
"Chaos—No Randomness in Cardiac Physiology," Kleen et al, Eur. Surg. Res., vol. 34 (2002), pp. 176-180.
"Influence of Atropine on Fractal and Complexity Measures of Heart Rate Variability," Perkiomaki et al, Ann. Noninvasive Electrocardiology, vol. 7 (Oct. 2002) pp. 326- 331.
"The Fractal Nature of Myocardial Blood Flow Emerges from a Whole-Organ Model of Arterial Network," Beard et al, J. Vasc. Res., vol. 37 (2000) pp. 282-296.

* cited by examiner

*Primary Examiner*—Brian Casler
*Assistant Examiner*—Elmer Chao
(74) *Attorney, Agent, or Firm*—Schiff Hardin LLP

(57) ABSTRACT

In a method and an apparatus for detecting the roughness of a vessel in a living subject, an in vivo image of an inner contour of the vessel wall is obtained using an imaging modality. A dimensional value characteristic of the complexity of the inner contour is calculated from the image information in the image describing the inner contour.

6 Claims, 3 Drawing Sheets

D=1, N=7

D = 1/2, N=23

D = 1/4, N= 61

D = 1/8, N=164

D = 1, N = 7

D = 1/2, N = 18

D = 1/4, N = 36

D = 1/8, N = 71

METHOD AND APPARATUS TO DETECT THE ROUGHNESS OF VESSELS

BACKGROUND OF THE INVENTION

The present invention concerns a method to detect the roughness of vessels, of the type wherein an inner contour of the vessel wall is acquired using an imaging modality.

The invention also concerns an apparatus to implement such a method.

Methods to detect vessel narrowings (stenoses) are necessary, for example for therapy for arteriosclerosis. In particular, a method is necessary with which the roughness of the inner vessel wall narrowed by arteriosclerosis can be gauged assessed. The roughness of the inner vessel walls also increases with progressing atherosclerosis.

Conventionally, the roughness of the arteriosclerotic deposit has been characterized with terms such as "complex" or "simple", as this is specified, for example, in chapter 1, "The Basics", page 2-5 of the book "Biostatistics" by G. R. Normal and D. L. Streiner, published by B. C. Decker, Hamilton, London, 2000. Such a dichotomous classification is unsuitable as a foundation for statistical evaluations. Viewed statistically, the generated data remain at a nominal level and are therefore only of limited use for studies. When a number of levels, for example "less", "moderate", "severe" are used for the characterization of the roughness of the arteriosclerotic deposits, the classification at best achieves an ordinal level. This is not sufficient, however, for statistical evaluations and studies that should form the basis for a therapy decision.

SUMMARY

An object of the present invention is to provide a method and an apparatus for quantitative detection of the roughness of arteriosclerotic deposits.

This object is achieved in accordance with the invention by a method wherein an inner contour of the vessel wall is initially acquired using an imaging modality, and a dimensional value characteristic of the complexity of the inner contour is then calculated from the acquired image information regarding the inner contour of the vessel wall.

To determine such a dimensional value characterizing the complexity of a curve, there are mathematical methods known to those skilled in the art that lead to reproducible results. In particular, a numerical value characterizing the complexity of the inner contour can be associated with a specific inner contour of a vessel wall using such methods. Data thus result on a ratio scale. Such data are particularly suitable for statistical evaluations and studies. Given the application of the method, it is therefore possible to acquire data that can serve as a basis for detailed studies. Such studies can then support therapy decisions.

In a preferred embodiment of the method, the determination of the dimensional value ensues by dividing the image of the contour line of the inner contour into fields and varying field measurement of these fields. The fields traversed by the contour line are numbered (enumerated), and the dimensional value is equal to the value of an exponent of a potential function describing the increase of the number of the enumerated fields with small, nascent field dimension. The result of this method is a dimensional value that is designated as a fractal dimension of the contour line of the inner contour.

This method offers the advantage that the decision as to whether a field is traversed by the contour line can be determined in a simple comparison of the coordinates of the stored image points of the contour line with the boundary coordinates of the fields. Given the frequently complex structure of arteriosclerotic deposits, this is a significant advantage in the determination of the dimensional value.

DESCRIPTION OF THE PREFERRED EMBODIMENTS

Figure 1A:
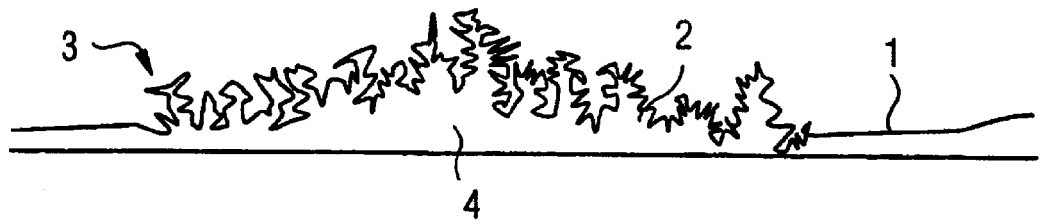
FIG. 1A through 1E are representations of an inner contour of a vessel wall, the dimensional value of which is determined by enumerating the fields covering the contour line at different field sizes in accordance with the invention.

FIG. 1A shows a contour line 1 of an arteriosclerotic deposit 2 that determines the inner contour 3 of a vessel wall 4.

The contour line 1 can be detected, for example, by introducing a contrast agent into the bloodstream and obtaining an x-ray exposure of the vessel to be examined is produced. Examination methods operating with intravascular ultrasound, with which resolutions up to 100 µm can be achieved, are a further possibility. The resolution of the exposure can be further improved using recently developed optical coherence tomography, which achieves resolutions in the range of 10 µm.

Figure 1B:
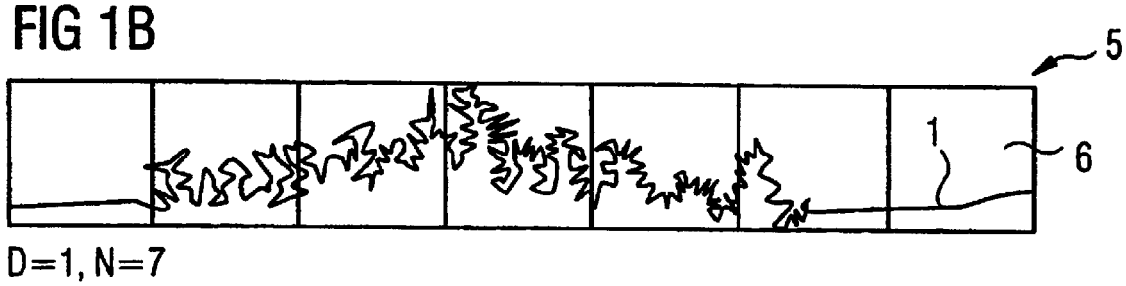

A first step to determine the fractal dimension of the contour line 1 is shown in FIG. 1B. In this method step, the contour line 1 has been covered by a rectangular surface 5 that has been divided into quadratic fields 6. The fields 6 exhibit a length D normalized to the numerical value 1. It can be seen from FIG. 1B that the contour line 1 passes through all seven fields 6.

Figure 1C:
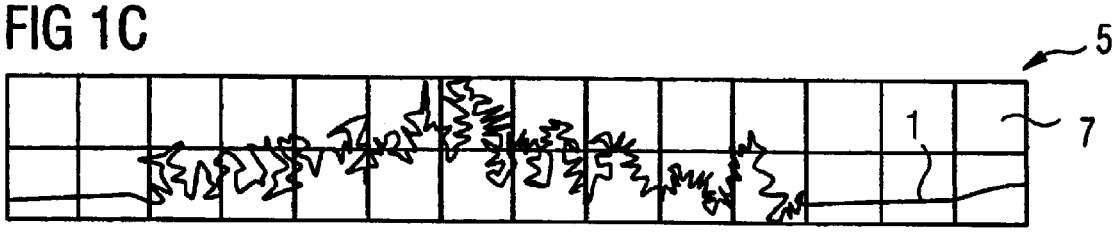

The field division of the area 5 has been refined in FIG. 1C. The area 5 is henceforth divided into fields 7 that exhibit an edge length with the value D=½. In the case of FIG. 1C, in total N=23 fields 7 are traversed by the contour line 1.

Figure 1D:
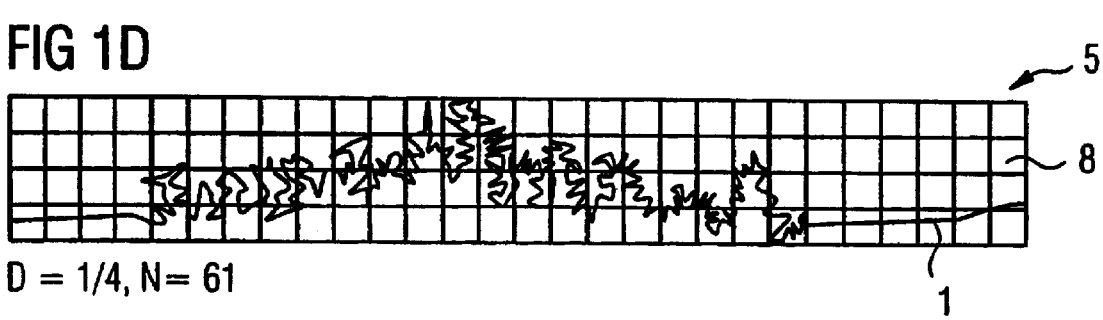
Figure 1E:
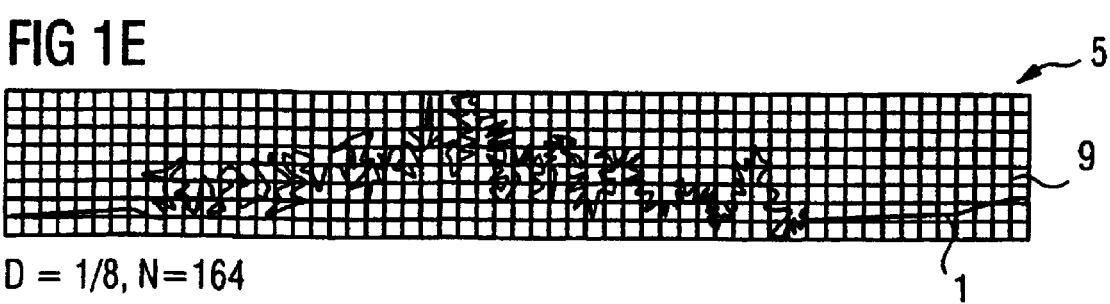

A further reduction of the field division has been effected in FIGS. 1D and 1E. In FIG. 1D, the edge length D of the fields 8 exhibits the value ¼, and in FIG. 1E the edge length D of the fields 8 exhibits the value ⅛. It can be seen from FIG. 1D that the contour line 1 in total passes through N=61 fields 8, while the contour line 1 in FIG. 1E traverses a total number of N=164 fields 9.

Figure 2:
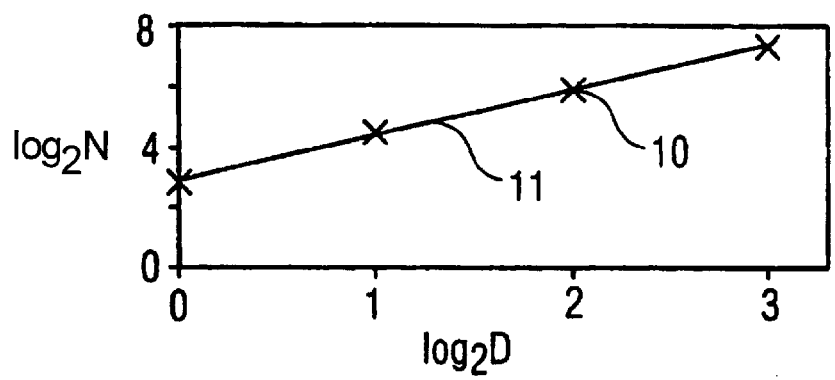
FIG. 2 is a graph from which can be read out the fractal dimension of the contour line from the slope of a function describing the connection between the field size and the contour line length in accordance with the invention.

The fractal dimension of the contour line 1 can be determined using FIG. 2. In FIG. 2, a dual-logarithmic graph is shown in which the logarithm of the number N of the fields traversed by the contour line 1 is plotted against the edge length D of the fields 6 through 9. Corresponding data points 10 are plotted in FIG. 2. The fractal dimension of the contour line 1 then results from the slope of a line of best fit 11 placed through the data points 10. In the case shown in FIG. 2, a fractal dimension of approximately 1.61 results for the contour line 1.

In comparison to the contour line 1, shown in FIGS. 3A through 3E each show a flatter contour line 12, the length of which Is determined in the FIGS. 3B through 3E at different field sizes via enumeration of the fields 6 through 9 covered by the contour line 12. Lengths of N=7, N=18, N=36 and N=71 respectively result in FIGS. 3B through 3E, whereby the edge lengths of the fields 6 through 9 respectively exhibit the value D=1, D=½, D=¼ and D=⅛. The result of the enumeration is shown in FIG. 4.

Figure 4:
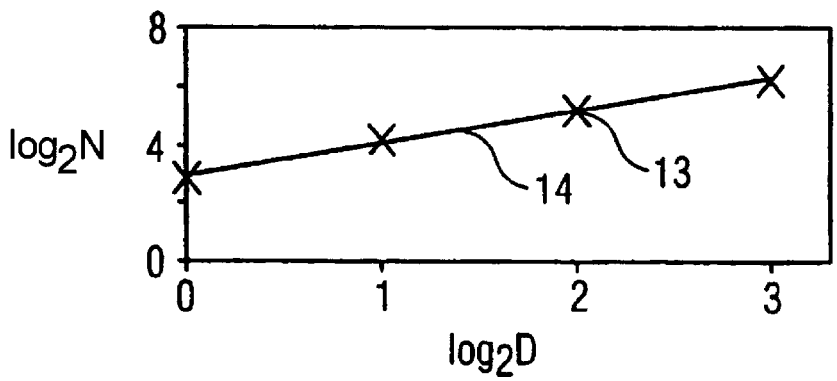
FIG. 4 is a graph corresponding to FIG. 2 to determine the fractal dimension of the contour line from FIGS. 3A through 3E in accordance with the invention.

FIG. 4 shows a dual-logarithmic diagram in which the logarithm of the number N of the enumerated fields is plotted against the logarithm of the edge length D of the fields 6 through 9. Data points 13 result to which a line of best fit 14 has been adapted. The slope of the line of best fit 14 is approximately 1.19, such that a fractal dimension of 1.19 can be associated with the contour line 12.

With the inventive method, it is possible to associate a numerical value (in the form of a fractal dimensional value) characterizing the roughness or complexity of the contour line 1 or 12 with the complexity or roughness of a contour line 1 or 12. By the association of a fractal dimensional value with a specific contour line, data result for the complexity of the contour lines that are suitable for statistical examinations. In particular, these data lie in an ordered value range that can be divided into identical intervals. The data on ratio scales obtained in this manner are particularly well suited for statistical analyses.

It is of particular advantage that the determination of the fractal dimension is independent of the image resolution and independent of the length of the examined contour line 1 or 12. Reproducible, comparable and statistically evaluable numbers thus result. The decision as to whether to use a stent or to conduct catheter-angioplasty to treat the atherosclerosis can then be judged on the basis of reliable clinical studies.

Figure 5:
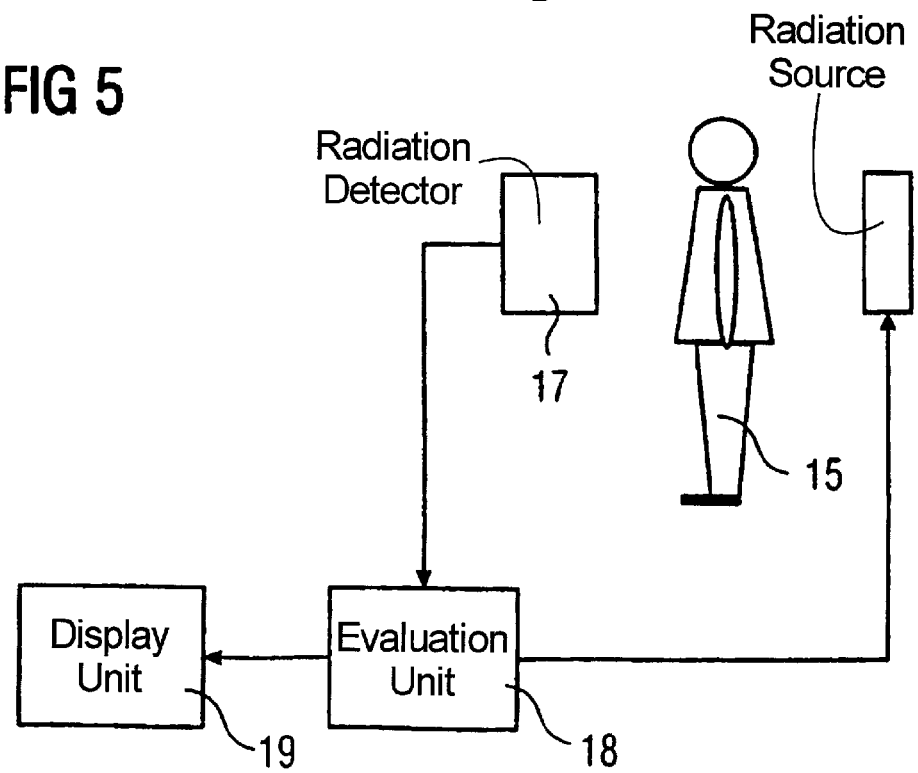
FIG. 5 is a schematic illustration of an apparatus to execute the method in accordance with the invention.
Figure 3A:
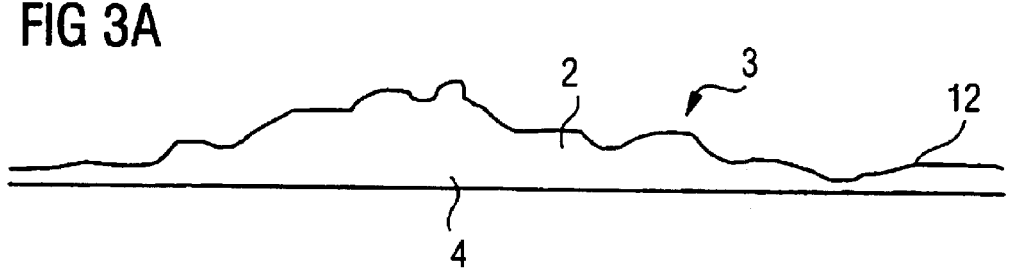
FIGS. 3A through 3E show flat (in comparison to the contour line shown in FIGS. 1A through 1E) contour lines, the dimensional value of which is determined corresponding to the contour lines shown in FIGS. 1A through 1E in accordance with the invention.
Figure 3B:
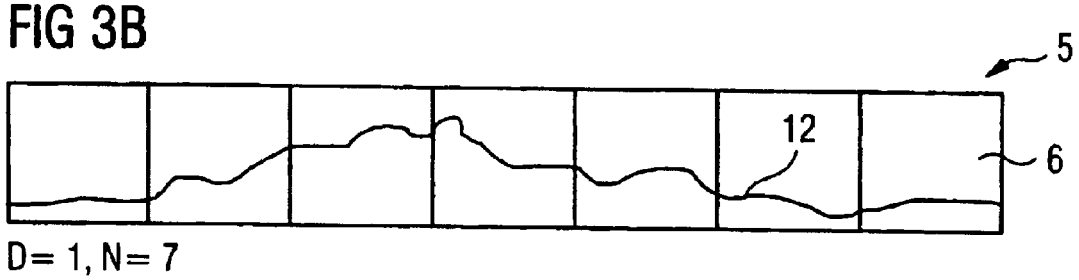
Figure 3C:
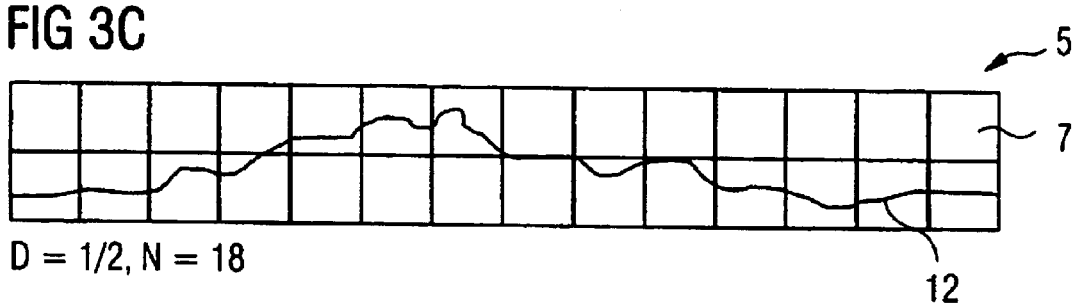
Figure 3D:
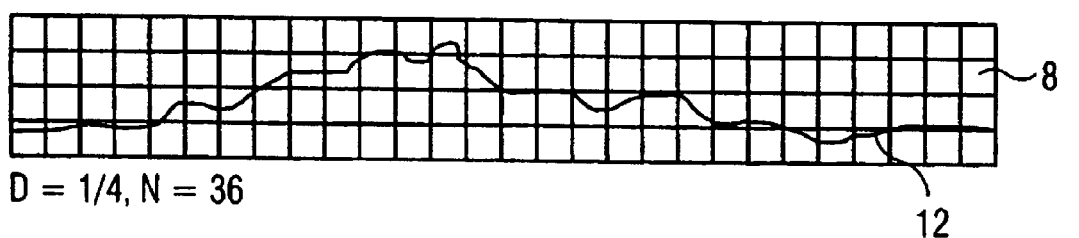
Figure 3E:
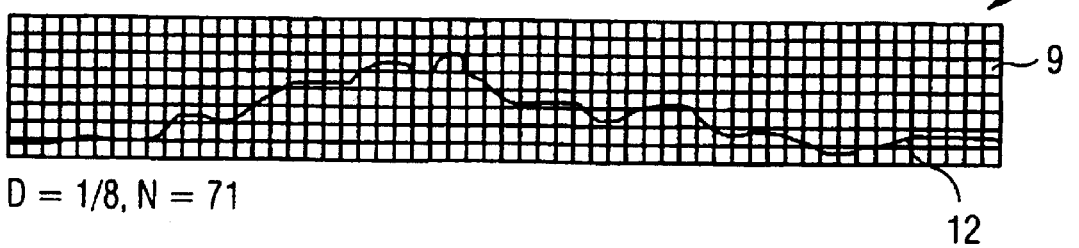

The basic components of an apparatus with which a vessel of a patient 15 can be examined is shown in FIG. 5.

An image of an inner contour 3 of a vessel of the patient 15 is acquired using a radiation source 16 and a radiation detector 17. The image is analyzed in an evaluation unit 18, and the result is output to a display unit 19.

The inventive method and apparatus are not limited to the determination of a contour line. It is also possible to detect a contour surface using a tomography modality and to detect its fractal dimension, the numerical values of which typically lie between 2 and 3.

It should also be noted that the inventive method and apparatus can be applied not only for arteries, but also to examination for any type of vessels in the body of a patient.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for detecting a roughness of a vessel situated in a living subject, comprising the steps of:
   providing a medical imaging modality;
   obtaining image data representing an image of an inner contour of a vessel wall of a vessel in the living subject using said imaging modality, said image containing image information representing a length associated with said inner contour; and
   supplying said image data to a processor and, in said processor, determining a dimensional value representing a complexity of said inner contour from said image information by analyzing said image information representing said length at increasingly finer resolutions and setting said dimensional value dependent on increase of said length, as said length represented by said image information increases upon analysis thereof at said increasingly finer resolutions, and making said dimensional value representing complexity of said contour available as an output from said processor at a display unit.

2. A method as claimed in claim 1 wherein the step of obtaining image data representing an image of said inner contour comprises obtaining image data representing an image of a contour line of said vessel wall.

3. A method as claimed in claim 2 wherein the step of determining said dimensional value comprises determining a dimensional value characteristic in a numerical range between 1 and 2.

4. A method as claimed in claim 1 wherein the step of obtaining image data representing an image of said inner contour of said vessel wall comprises obtaining image data representing an image of a contour line of a cross-section of said vessel.

5. A method as claimed in claim 2 wherein the step of determining said dimensional value comprises dividing said image of said contour line represented by said image data into a plurality of fields of equal size, varying the size of said fields by successively decreasing said size, determining, for each variation, an increase in a number of said fields traversed by said contour line, and setting said dimensional value as being equal to an exponent of a potential function describing said increase.

6. An apparatus for detecting a roughness of a vessel in a living subject, comprising:
   an imaging modality for acquiring an image of an inner contour of a vessel wall of a vessel in the living subject, said image containing image information representing a length associated said inner contour; and
   an evaluation device configured to determine and display a dimensional value characteristic from said image information representing a complexity of said inner contour by analyzing said image information representing said length at increasingly finer resolutions and setting said dimensional value dependent on said length, as said length represented by said image information increases upon analysis thereof at said increasingly finer resolutions.

* * * * *